United States Patent [19]

Vardoulakis et al.

[11] Patent Number: 4,825,700
[45] Date of Patent: May 2, 1989

[54] BI-AXIAL GEOMATERIAL TEST SYSTEM

[75] Inventors: Ioannis G. Vardoulakis, Minneapolis; Andrzej Drescher, New Brighton, both of Minn.

[73] Assignee: Regents of the University of Minnesota, Minneapolis, Minn.

[21] Appl. No.: 207,148

[22] Filed: Jun. 15, 1988

[51] Int. Cl.[4] ............................................. G01N 3/24
[52] U.S. Cl. ...................................... 73/749; 73/819; 73/845
[58] Field of Search ................. 73/845, 819, 795, 821, 73/790, 794, 818, 822, 823, 825

[56] References Cited

U.S. PATENT DOCUMENTS

| | | | |
|---|---|---|---|
| 3,199,341 | 8/1965 | Heuer, Jr. et al. | 73/94 |
| 3,505,860 | 4/1970 | Bishop et al. | 73/94 |
| 3,616,685 | 11/1971 | Strom | 73/84 |
| 4,047,425 | 9/1977 | Handy et al. | 73/94 |
| 4,122,704 | 10/1978 | Lutenegger et al. | 73/822 |
| 4,539,851 | 9/1985 | Lutenegger | 73/845 |
| 4,562,726 | 1/1986 | Barnaby | 73/38 |
| 4,594,899 | 6/1986 | Henke et al. | 73/784 |
| 4,599,891 | 7/1986 | Brauer et al. | 73/38 |
| 4,649,741 | 3/1987 | Strom | 73/84 |

Primary Examiner—Jerry W. Myracle
Attorney, Agent, or Firm—Kinney & Lange

[57] ABSTRACT

A bi-axial compression test apparatus for geomaterial (soil, etc.) samples that is designed to allow free shear band formation and provide measurements of the stress displacement characteristics of the failure zone. A geomaterial sample formed into a specimen comprising a right rectangular prism is surrounded by a thin rubber membrane and is supported by walls along two parallel faces. An axial load is kinematically applied by a plate that is guided to prevent any tilt or eccentricity, while a bottom support plate for the specimen is horizontally guided by a linear bearing that is substantially friction free. All of the surfaces in contact with the specimen are glass lined and lubricated to minimize friction. The assembly of the specimen and its supports is placed in a conventional tri-axial cell in a loading frame so that an axial load can be applied to one end of the specimen and reacted against the bottom plate. Internal loaded load cells allow for accurate measurement of the axial force, and any eccentricities thereof, as well as friction along the side walls. Displacement transducers monitor the axial and lateral displacements of the specimen and the horizontal movement of the bottom plate, to permit analysis of the shear mode, and when to determine shear failure occurs.

15 Claims, 4 Drawing Sheets

BI-AXIAL GEOMATERIAL TEST SYSTEM

The inventor wishes to acknowledge support of the state of Minnesota and of the National Science Foundation under Grant No. NSF/CEE-8406500. The U.S. government has certain rights to this invention.

BACKGROUND OF THE INVENTION

1. Field of the Invention

The present invention relates to a bi-axial test apparatus which permits testing samples of geomaterials under axial loads while continuously monitoring the axial force, axial and lateral displacement and translation of a base supporting the sample.

2. Description of the Prior Art

Bi-axial testing of geomaterial, which, for purposes of this application, is defined as including, but not limited to soil, sand, rock, ceramics, concrete, snow and ice, has been recognized as important in determination of geomaterial characteristics. Bi-axial testing has been carried out in the prior art, as reported by I. Vardoulakis and M. Goldscheider in a publication entitled "Biaxial Apparatus for Testing Shear Bands in Soils", presented at a conference in Stockholm in 1981. (I. Vardoulakis and M. Goldscheider (1981). Biaxial Apparatus for Testing Shear Bands in Soils. X ICSMFE, Stockholm, 4/61, 819-824).

The experimental apparatus disclosed therein utilized a specimen support plate that was mounted on rollers, as is shown in FIG. 5 of the publication, and wherein the loads were applied by an axial piston force acting on the soil sample in a longitudinal direction, while the sample was permitted to shear and laterally displace in one axis as it was loaded. The sample or specimen was enclosed in a rubber membrane. Eccentric loading and friction, particularly in relation to the mounting of the specimen support base, and the inability to determine displacement along the axial length of the specimen as it was being loaded limited its applicability.

Various tri-axial test devices have been advanced and also are well known. It also is known to encase geomaterial samples in outer membranes and surround the sample with a fluid under a desired hydrostatic pressure in a chamber during the loading. Such a device, in simplifed form, is shown in U.S. Pat. No. 3,616,685. The device shown in the above-identified Vardoulakis article also included an outer confining pressure housing. Generally, in tri-axial testing of samples the lateral pressures generated by axial loads in the specimen are of interest. U.S. Pat. Nos. 4,047,425; 4,599,891; and 4,122,704 illustrate such devices.

SUMMARY OF THE INVENTION

The present invention relates to apparatus for biaxially loading a geomaterial sample that is preferably formed into a rectangular prism specimen which has an outer rubber membrane or cover, and which is then subjected to an axial load under controlled conditions while the sample is supported in a manner to permit bi-axial displacement. The specimen is loaded along a longitudinal axis from one end and is slidably retained from displacement from along two parallel sides while permitting displacement along a second axis parallel to the two sides and perpendicular to the longitudinal axis. The specimen movements or displacements in the two axes are monitored closely with displacement sensors (LVDTs) so that as the specimen is loaded to failure the shear band can be detected.

The specimen is loaded by a conventional test loading ram against a base plate that is mounted on very low friction guideways which permit the plate to move parallel to the second axis and thus parallel to the two sides of the specimen that are constrained. The amount of movement of the plate along the guideways during the loading of the specimen is also monitored. By determining the relative movement of the specimen at various locations along the longitudinal axis of the specimen, the specimen can be analyzed to insure accurate interpretation of the results of loading.

Additionally, load cells for measuring the load applied are mounted in the base plate. The load direction is nominally centered on the longitudinal axis of the specimen. The load cells are arranged to determine any eccentricity of the load relative to the longitudinal axis of the specimen during the test. The load cells also provide a way of determining friction losses by comparing the loads sensed by the load cells at the base plate supporting the specimen, with the load actually applied to the specimen with the loading ram, which is measured by a separate load cell. The surfaces of the constraining members for the test specimen are all lined with glass to minimize friction, and are also lubricated with silicone-based lubricants. By analysis of the various measurements, including the load applied, the eccentricity of the load, the friction losses along the side walls retaining the specimen, and the measurements from the displacement transducers that monitor the axial and lateral displacements of the specimen, as well as the horizontal movement of the base plate supporting the specimen, a full and accurate evaluation of the formation of planar shear bands in the particular geomaterial, sample or specimen being tested can be obtained.

DETAILED DESCRIPTION OF THE PREFERRED EMBODIMENTS

Figure 1:
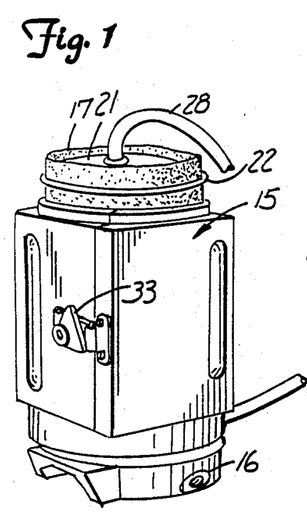
FIG. 1 is a part perspective and schematic view of a mold used for forming a specimen inside a thin outer membrane that will be used during the test, and showing the mold being assembled in position on specimen backing plates.
Figure 2:
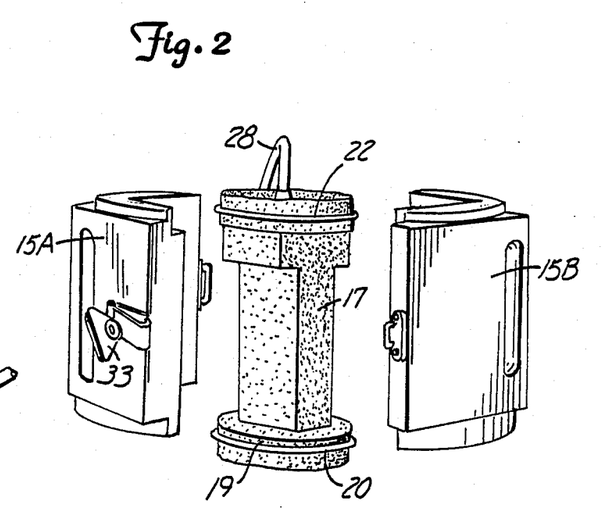
FIG. 2 is a perspective view of a typical specimen encased within a mold after forming.
Figure 4:
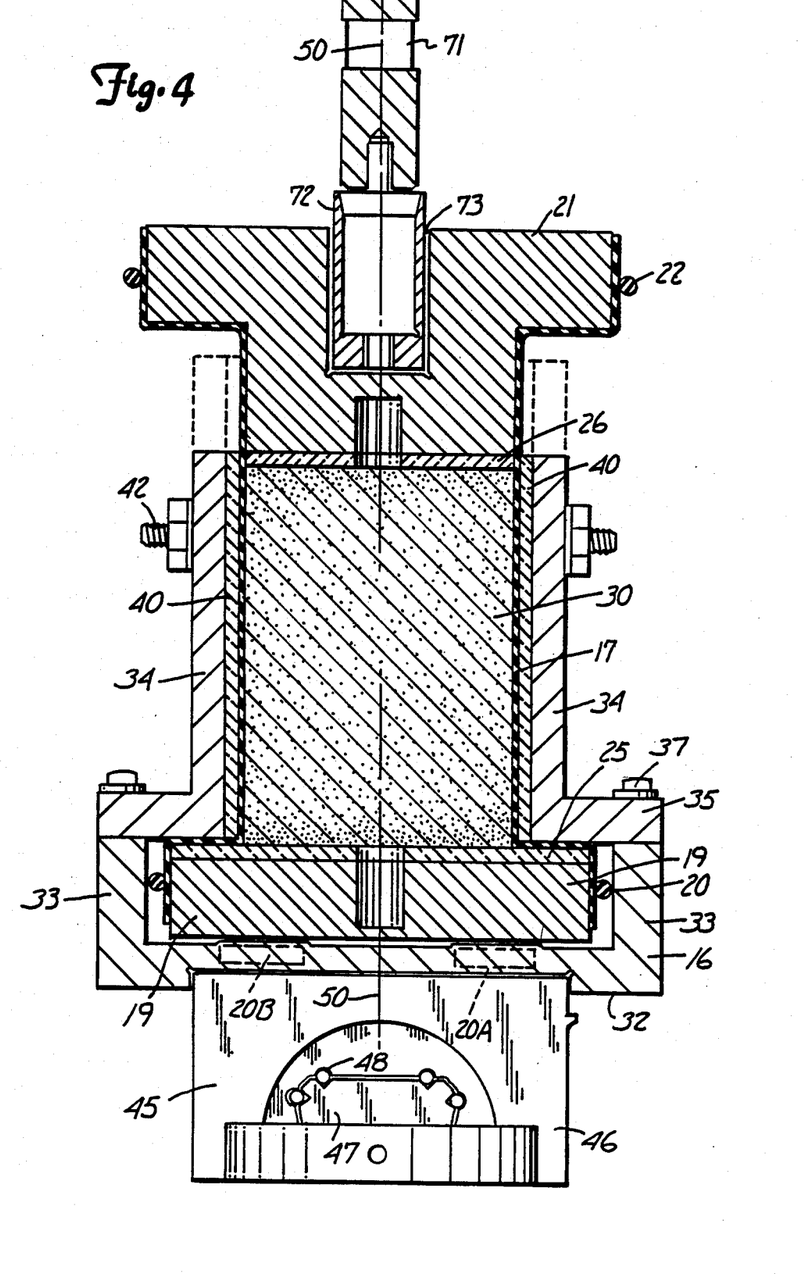
FIG. 4 is a vertical sectional view through a specimen, in place on the machine in FIG. 3 and illustrating the arrangements for counting the specimen between glass lined side walls that rigidify the specimen in two directions.

The process and apparatus for forming a suitable geomaterial specimen will be discussed first, and is schematically shown in FIGS. 1 and 2. An outer mold indicated generally at 15 is made of a suitable plastic material and is made in two sections 15A and 15B as shown in FIG. 2, where it is disassembled from the specimen. The mold sections are assembled and mounted in place on a test specimen bottom support plate or base member 16. The mold sections 15A and 15B are clamped together, and define an interior chamber having a cross-section that is desired for the specimen. As shown, the specimen is prismatic. A rubber membrane or sleeve 17 is placed in the interior of the mold, and is fastened to a lower specimen support 19 which has a circular outer periphery section, which is connected to the square end block that fits partially into the mold and directly suports the specimen. An O-ring 20 is placed around the outer periphery of this lower support to hold the membrane 17. The space enclosed by the rubber membrane 17 is then filled with materials from its upper end, and these materials are formed to reach a desired density. In the preferred form, the geomaterial sample was sand. An upper specimen support 21 is placed in position at the upper end of the mold 15, with the mold sections assembled, and an O-ring 22 is placed around the rubber membrane 17 at the periphery of the upper specimen support 21 to hold the membrane 17 in place on the upper specimen support. Both the upper specimen support 21 and the specimen base 19 have glass lining plates thereon that line the sides that face the specimen, as can be seen in FIG. 4. These glass lining plates include a glass lining plate 25 on the lower specimen support 19, and a glass lining plate 26 on the upper specimen support 21.

Both the upper specimen support 21 and the lower specimen support 19, and the respective glass plates have apertures therein for attaching vacuum hoses shown at 28, that are connected to a suitable vacuum source to subject the specimen to a vacuum as it is formed and tightly pack the geomaterial (soil) to form the specimen inside the membrane 17. Material can be filled into the space enclosed by the membrane and packed in, and the vacuum applied for packing. The steps of filling, packing and using vacuum can be repeated until the specimen is suitably formed. Once the desired specimen density has been achieved due to differential pressure, upper specimen support 21 is put in position and the formed specimen indicated generally at 30 in FIG. 4 is properly shaped and is surrounded by the membrane 17, which tightly adheres to the surfaces of the specimen. The apertures in the upper and lower glass plates also permit drainage of pore water from the specimen.

The mold sections 15A and 15B are released after forming the specimen using a suitable release clasp as indicated generally at 33. There is a hook or other fastener on the diagonally opposite corner of the mold sections from that shown in FIG. 2 which permits release of the molds, and the specimen then will be resting in position on the lower specimen support 19 and bottom support plate 16, which can then be assembled into the test apparatus for bi-axial testing of the geomaterial sample formed into a specimen. The formation of the specimen follows generally known techniques and is not part of the present invention.

Figure 8:
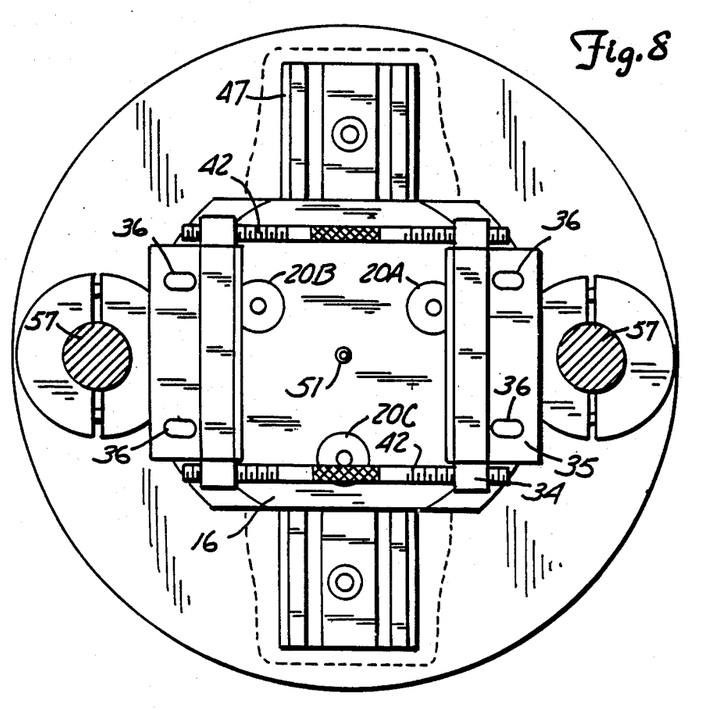
FIG. 8 is a top plan view of the apparatus of FIG. 1 generally along the line of section 5—5 with the specimen removed for showing the mounting of the mechanical elements utilized with the present invention.

The specimen is then ready to mount in the test apparatus. The bottom support plate or base 16, as perhaps can be best seen in FIGS. 4 and 8, has a bottom wall 32, and a pair of diametrically opposite, part annular side guide walls 33 extend only partially around the lower specimen support 19. The part annular guide walls 33 have part cylindrical inner surfaces that are of size to receive the lower specimen support 19, which has a cylindrical periphery with O-ring 20 thereon. The side guide walls 33 are provided with flat and parallel upper surfaces on which a pair of specimen retaining side plates 34 are mounted, respectively. The side plates 34,34 have bases 35 that are at right angles to the plane of the side plates 34, and the bases 35 are provided with slots 36 therethrough as seen in FIG. 8, for receiving cap screws 37 that thread into the upper surfaces of guide walls 33 and hold the respective side plates 34 rigidly attached to the bottom support plate 16. The side plates 34,34 are lined with glass plates 40 which bear against the outer side surfaces of the membrane 17, in which the specimen 30 is formed. A layer of silicone grease or other lubricant is placed between the smooth glass plates 40 (and 25 and 26 at the top and bottom) and the rubber membrane 17 retaining the specimen 30, to minimize friction between the specimen carrying membrane 17 and the side plates 34. The side plates 34 constrain the specimen and do not permit movement of the specimen in direction perpendicular to the surfaces of the side plates.

The side plates 34 are connected together and restrained with tie rods 42 that extend through provided slots formed by ears on the sides of each of the side plates 34. The tie rods 42 can be threadably adjusted to control the spacing of the side plates. The tie rods 42 span the width of the specimen and are spaced outwardly from the adjacent surfaces of the specimen 30 that are at right angles to the specimen surfaces that engage the glass plates 40 on side plates 34. The tie rods 42 are adjusted to position the side plates 34 at the correct spacing for maintaining the contiguous side surfaces of the specimen 30 in desired planes and to resist the components of specimen loading forces acting perpendicular to the inner surfaces of the side plates. While one tie rod 42 is shown, there generally are at least two such tie rods on each of the sides of the specimen perpendicular to the surfaces of plates 34 during use. The tie rods 42 can be adjusted to control the lateral side pressure on the specimen prior to applying the longitudinal axial load on the specimen.

The side plates 34 provide a rigid form to resist extrusion or movement of the specimen laterally in direction perpendicular to the plane of these plates.

The assembly of the bottom support plate or base 16, the side plates 34, and the specimen 30 mounted in the outer membrane 17 is then placed on a linear slide assembly indicated generally at 45, which is a commercially available unit, that is made to provide a very low coefficient of friction sliding support for the specimen bottom support plate or base 16. The specimen thus can readily and easily slide in directions along the axis of the linear slide assembly 45. As shown, the linear side assembly has a sliding movable member 46 mounted onto a rail 47 with suitable ball supports 48 mounted in raceways formed in the rail 47 and in the mating surface of the sliding member 46. Thus, the bottom support plate 16 and the slide assembly 45 provide substantially friction-free sliding movement in direction parallel to the plane of the side plates 34 and perpendicular to the supported upper and lower end surfaces of the specimen 30.

The lower specimen support 19 is directly supported on three load cells, indicated generally at 20A, 20B and 20C, respectively, that are mounted in the bottom wall 32 of the bottom support plate 16. The loads cells 20A–20C have load cell buttons that support the bottom surface of the lower specimen support 19 slightly spaced from bottom wall 32. The positions of these load cells in relation to the central longitudinal axis 50 of the specimen (which is the desired axis of loading) and the lower specimen support is such that any eccentricity in axial load relative to the central axis 50 can be determined by taking the load readings from the individual load cells 20A–20C. Central axis 50 is coincident with the central line or axis of a locating pin 51 that fits into a receptacle in the bottom of the lower specimen support 19. The locating pin 51 is used for locating the lower specimen support 19 in the bottom support plate 16 prior to the time that the side retainer plates 34,34 are put into place.

Once the assembly of the specimen, side plates 34 and bottom support plate 16 has been made, the bottom support plate 16 is placed on the linear slide assembly 45, which is mounted permanently in a load frame indicated generally at 55. The load frame permits applying an axial load, parallel to the axis 50, on the specimen 30.

The load frame includes a base 56, and a pair of upright precision ground columns 57 that are fixed to the base 56. Columns 57 are spaced apart so that the linear slide assembly 45 fits between the columns, and the lower specimen base 16, specimen 30, side plates 34, and the top specimen support 21 will also fit between the columns. An upper guide bar or crosshead 60 is slidably mounted on suitable ball bushings 61 that are in turn mounted on the columns 57, so that the upper guide bar will freely slide axially, in direction along the axis 50, as well as along the axes of the columns 57, which are parallel to the axis 50.

An upper guide bar limit screw indicated at 65 is threadably mounted through a connecting bar 66 that is fixed to the top of the columns 57. The screw 65 controls the position of the guide bar or cross head 60 axially along columns 57. The guide bar 60 in turn has a central opening therein in which a guide bushing 67 is mounted, and the guide bushing 67 also mounts a ball bushing 68 that slidably mounts a loading shaft assembly 70.

The loading shaft assembly 70 includes a load cell 71 that is positioned below the guide bar 60. The load cell 71 has a coupling end 72 that fits within a receptacle 73 on the specimen top support 21. The load cell 71 is used for applying and measuring compressive load against the specimen top support 21 in a known manner. Thus the load cell measures the load applied axially onto the specimen 30 during the test sequence.

A loading ram screw 75 is positioned so that it will bear against the hardened end or nut 76 on the shaft assembly 70. The loading ram screw 75 is operated through a suitable mechanical actuator indicated schematically at 80 for a conventional tri-axial cell test frame. This actuator can be any type of desired actuator, so long as an axial compression load can be applied to the shaft 70 and in turn through the load cell 71 to the specimen top support 21.

In addition to monitoring the axial loads that are applied, using the load cell 71, it is important to determine when the specimen 30 fails along a shear plane from this axial load. In order to determine when and where failure occurs, a number of displacement sensors are mounted to sense shifting of upper and lower portions of the specimen 30, and also the shifting of the bottom support plate 16 in direction along the axis of the linear slide rail 47. The movement of the specimen top support 21 in direction of axis 50 as the specimen is loaded is also sensed by linear displacement sensors, or LVDTs.

Figure 5:
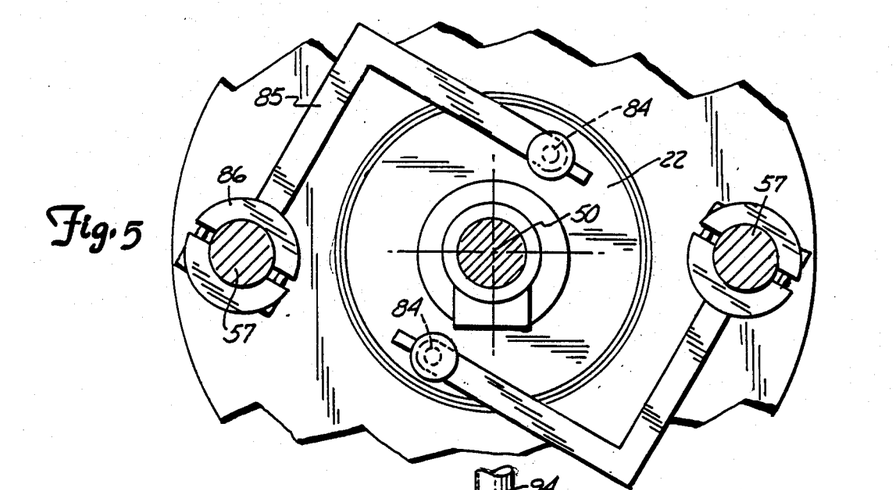
FIG. 5 is a sectional view taken as on line 5—5 in FIG. 3.

As shown in FIGS. 4 and 5, a pair of LVDTs (linear displacement sensors) 84,84 are positioned on opposite sides of the central axis 50 and diametrically opposed, and are positioned above the specimen top support 21. These LVDTs 84 are mounted on arms 85 that extend from the respective columns or shafts 57. The arms 85 are held in place on the columns or shafts 57 with suitable split collars 86. The LVDTs 84 have sensing shafts 88 that are parallel to axis 50 and which extend down and engage the top surface of the specimen top support 21. The sensing shafts 88 are sensitive to linear motion and the LVDTs provide output signals proportional to such motion. Comparison of the signals from the LVDTs 84 will indicate if the specimen top support 21 is tilting slightly under load, and also the signals can be used for determining movement of the upper portions of the specimen 30 under compression loading. The indications of movement or displacement can be correlated to the loads being sensed by load cell 70 (and by load cells 20A, 20B and 20C) for analyzing the specimen properties.

Figure 3:
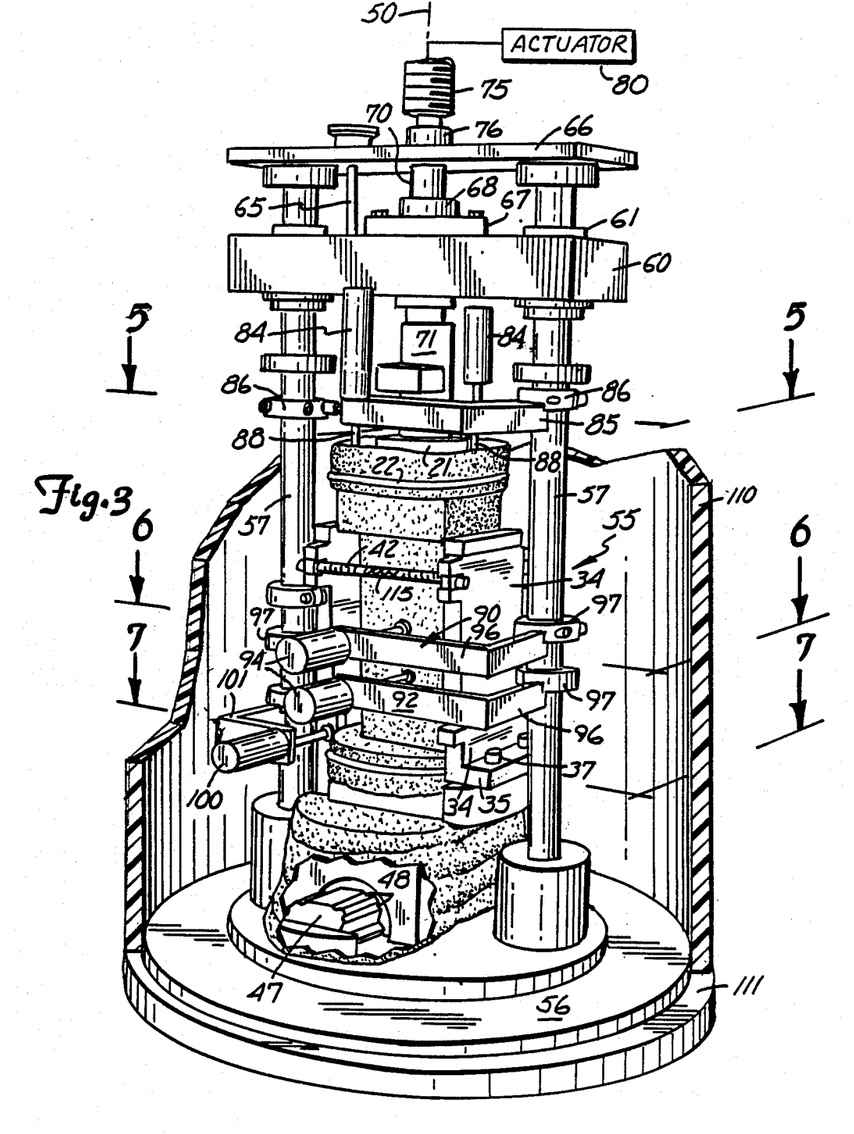
FIG. 3 is a perspective view of a testing apparatus showing the specimen of the present invention installed therein.

In order to determine lateral displacements of different portions of the specimen along a shear plane as the specimen is loaded axially, the unrestrained or unsupported side surfaces of the specimen (at right angles to the supported surfaces contiguous to plates 34) are sensed with displacement sensors (LVDTs at two (or more)) different levels on the specimen. The displacement sensors can be shifted axially (in direction along axis 50) to desired positions. As shown in FIG. 3, there is an upper set of displacement sensors (LVDTs) indicated generally at 90 and a lower set of displacements sensors indicated generally at 92 that are identically constructed, but that are axially displaced so that the amount of movement of the specimen at two different levels can be determined.

Figure 6:
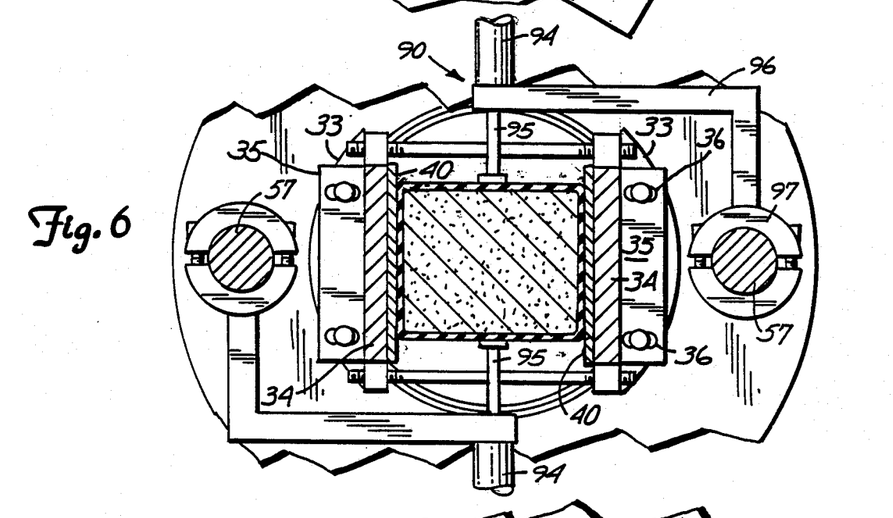
FIG. 6 is a sectional view taken as on line 6—6 in FIG. 3.

As shown at FIG. 6, the set of displacement sensors 90 comprise LVDTs or linear displacement sensors 94,94 at both the front and rear sides of the specimen, and have contact shaft members 95 that engage the unconstrained front and rear side surfaces of the specimen 30, respectively. The displacement sensors 94 are supported on suitable support arms 96 utilizing split collars or clamps 97 that attach to the columns or shafts 57. The displacement sensors 94 can be adjusted to the desired level along the axis 50. The displacement sensors 94 of the set 90 are mounted on the same plane extending perpendicular to the axis 50. Thus the outputs from the opposite side displacement sensors 94 will detect shifts of the specimen 30 in direction parallel to the restraining surfaces of the low friction glass plates 40 on side plates 34.

The set of displacement sensors shown at 92 include two displacement sensors 94, and arms 96, as well, but that are at a lower level on the specimen 30 as shown in FIG. 3.

Figure 7:
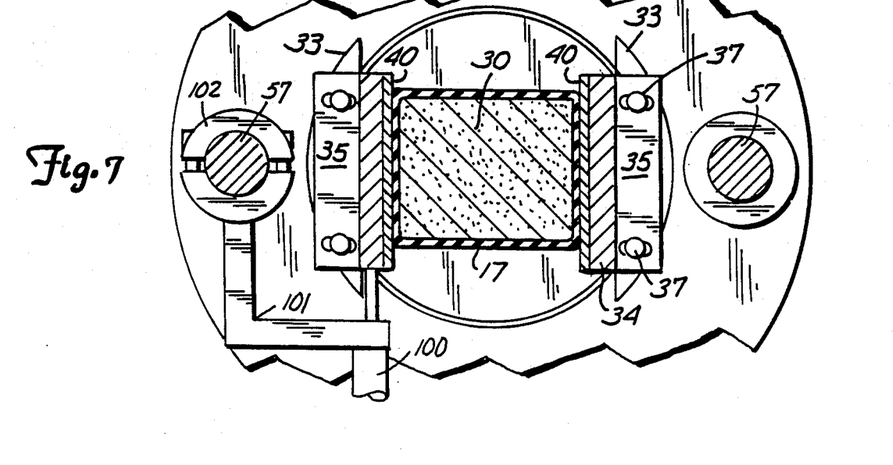
FIG. 7 is a sectional view taken as on line 7—7 in FIG. 3.

For analyzing the load and movements involved in testing a geomaterial sample comprising a specimen, the position of the bottom support plate 16 in direction along the axis of the linear slide assembly 45 also is sensed utilizing a displacement sensor or LVDT 100 that is mounted onto an arm 101, (FIGS. 3 and 7) which has a collar or clamp 102 that clamps onto one of the columns or shafts 57. The sliding of the bottom support plate 16 from a reference portion will indicate a shear failure of the specimen under axial compression loading of the specimen 30.

Tests are usually conducted with the entire specimen 30, and the loading assembly, including the side plates 34, the bottom plate 16, and the linear slide assembly 45, as well as the load and guide frame 55, inside a pressure vessel, which permits a hydrostatic pressure to be applied to all sides of the specimen to prevent failures which are not attributable to shear failures. The pressure vessel 110 is a plexiglass cylinder, which seats down onto a shoulder 111 on the base 56, and can be sealed therewith thereon with suitable O-rings. An upper plate is used to seal the pressure vessel 110 in a known manner and then the vessel 110 can be filled with oil and placed under a pressure, for example in the range of up to eight atmospheres. The loading ram is sealed with respect to the top plate of the vessel so it can provide a load through the top plate in a convention manner. The pressure can be regulated in a manner presently known and used for testing geomaterial samples, and does not form part of the present invention, in that it is conventionally done for testing purposes.

Each of the individual load cells, namely load cell 71 at the top of the specimen and load cells 20A, 20B and 20C at the bottom, will provide an output electrical signal to suitable controls. Each LVDT also will provide an output signal to the controls, so that the inputs as to load, and each of the signals from the displacement sensors as to displacement, can be correlated to determine the loading conditions and specimen failure conditions. The friction present along the support and constraining surfaces engaging the specimen 30 can be determined by determining the applied load from the load cell 71, for example, along the axis 50, and the load on the lower specimen support sensed by the load cells 20A-20C, and subtracting the two figures. Friction losses can easily be calculated. The tests can be conducted in a suitable manner to obtain the information desired. The results can be analyzed.

The positioning of the load cells 20A-20C on the bottom wall 32 of the bottom support plate 16 in relation to the central axis 50 is such that any eccentricity of loading relative to the central axis 50 can be determined.

As the axial force along axis 50 increases, tending to axially compress the specimen, the amount of shifting of the specimen in the longitudinal axial direction can be sensed by the displacement sensors or LVDTs 84. Any tendancy of the bottom support plate 16 to slide as the specimen 30 fails in shear will be sensed by the LVDT 100 that has an indicator shaft which rests against an edge portion of the bottom support plate 16 to sense its movement in directions along the axis of the support rail 46. As the specimen 30 starts to fail along a shear plane, one portion of the specimen 30 will tend to shift laterally of its longitudinal axis relative to other portions in a direction parallel to the planes of the surfaces of the restraining plates 34 and the glass lining plates 40 thereon. This shifting will be sensed by the LVDTs 94, and the respective sets of LVDTs 90 and 92, that are at different levels on the specimen. Complete failure can be determined by the amount of shifting of the bottom support plate 16, as sensed by the LVDT 100 or by the amount of shifting of the specimen 30 itself as sensed by the LVDT sets 90 and 92. The shear plane failure at an angle with respect to axis 50 is generally as shown in the prior art article mentioned in the Background of the Invention. That article also discusses the types of tests and test theory involved. The general orientation of the failure shear plan is indicated by dotted lines in FIG. 2 at 120 for illustrative purposes. The upper and lower portions of the specimen shift relative to each other when shear failure occurs.

The lateral pressure tending to separate the rigid support plates 34 perpendicular to the surfaces of the support plates can be measured by providing strain gauges or sensors indicated generally at 115 on the tie rods 42.

The low friction glass plates 40 on the plates 34 and at the top and bottom of the specimen used for contacting the membrane 17 can be polished smooth, and any scratches or other imperfections can be easily seen and polished down so they do not tend to increase the resistance to shifting of the specimen. The test loads can be carefully controlled, and the low friction slide assembly 45 insures that the loading of the specimen 30 will be unaffected by binding or friction loads of the bottom support plate 16.

Although the present invention has been described with reference to preferred embodiments, workers skilled in the art will recognize that changes may be made in form and detail without departing from the spirit and scope of the invention.

What is claimed is:

1. In a bi-axial test apparatus for testing geomaterial samples for failure under load in direction generally along a central axis of the specimen, for a specimen with top and bottom end surfaces, and four side surfaces, forming a generally rectilinear cross section configuration, comprising a bottom support plate supporting a bottom end surface of said specimen, a pair of side plates at two opposite side surfaces of the specimen for restraining movement of the specimen in first lateral directions perpendicular to the axis, the specimen being loaded being substantially unrestrained from shifting in direction parallel to the side plates, means to load such specimen on a top end surface under a load directed toward the bottom support plate axially along such specimen until the specimen fails in shear and at least two portions of such specimen shift in a direction parallel to the side plates, the improvement comprising glass surfaces on the side plates for engaging a specimen to be tested.

2. The apparatus as specified in claim 1 and low friction linear slide means for mounting the bottom support plate for movement along a linear support substantially axis parallel to the planes of the side plates.

3. The apparatus as specified in claim 2 and first displacement sensor means for sensing displacements of said bottom support plate in direction along the axis of the linear slide means, and second linear displacement means engaging at least one side surface of a specimen to be tested that is generally perpendicular to the plane of the side plates at two different axially spaced locations to determine differential movements between at least two portions of a specimen being tested.

4. The apparatus as specified in claim 2 and a plurality of load cells supported on the linear slide means for measuring the load on a specimen transferred to the bottom support plate, said load cells being arranged at a known relationship to, but spaced from the central axis to indicate eccentricity of the center of loading relative to the central axis.

5. The apparatus of claim 4 and a primary load cell for measuring the load applied to the top end plate engaging a specimen being tested, the friction that is present between the specimen and the side plates thereby being capable of being determined by measuring the differential in load at the load cells supported on the linear slide means and the primary load cell.

6. The apparatus as specified in claim 5 and third displacement sensing means for measuring the displacement of said bottom support plate along the support linear axis.

7. The apparatus as specified in claim 6 and fourth displacement sensing means for sensing the displacement of the top end plate of a specimen in direction along the central axis.

8. The apparatus as specified in claim 1 in combination with a specimen mounted between the side plates, a top end plate engaging the top end surface of the specimen, said specimen being surrounded by an elastic membrane that is sealed with respect to the bottom support plate and the top end plate, and a load cell for measuring the loads applied to the top end plate.

9. A bi-axial test apparatus for testing geomaterial sample specimens for failure under load in direction generally along a central axis of the specimen, which has first and second end surfaces, and a pair of generally parallel side surfaces, comprising a support plate supporting a first end surface of said specimen, a pair of side plates fixedly mounted relative to the bottom support plate for restraining movement of the parallel side surfaces of a specimen to be tested in a first lateral direction perpendicular to the axis of loading the specimen being tested being substantially unrestrained from shifting in directions parallel to the side plates, means for loading such specimen on a second end surface under a load directed toward the support plate along the central axis of the specimen until such specimen fails, and means for supporting the support plate for movement relative to the means for loading along a support axis parallel to the parallel surfaces of such specimen and perpendicular to the loading direction comprising a ball bearing supported slide member that provides friction free movement of the support plate relative to the means for loading.

10. The apparatus as specified in claim 9 and displacement sensor means for sensing displacements of said support plate in direction along the support axis, and further linear displacement means engaging at least one side surface of a specimen to be tested other than the parallel side surfaces at two different axially spaced locations to determine differential movements under shear between at least two portions of a specimen being tested.

11. The apparatus as specified in claim 9 and a plurality of load cells mounted plate for measuring the load on a specimen transferred to the support plate, said load cells being arranged at a known relationship to, but spaced from the central axis of the specimen to indicate eccentricity of loading relative thereto.

12. The apparatus of claim 11 and a primary load cell for measuring the load applied to a first end of a specimen being tested, the friction that is present between the specimen and the side plates thereby being capable of being detetermined by measuring the differential in loads from the load cells associated with the support plate and the primary load cell.

13. The apparatus as specified in claim 9 and a third displacement sensing means for measuring the displacement of said support plate along the support axis.

14. A bi-axial test apparatus for testing a geomaterial specimen for failure under load in direction generally along a central axis of such specimen comprising a bottom support plate supporting a bottom end surface of such specimen, a pair of side plates at two opposite side surfaces of the specimen for restraining movement of the specimen in first lateral directions perpendicular to the central axis, the specimen being loaded being substantially unrestrained from shifting in directions parallel to the side plates, means to load such specimen on a top end surface under a load directed toward the bottom support plate in direction of the central axis of such specimen until the specimen fails in shear, and a plurality of load cells supported on the apparatus for measuring the load on a specimen transferred to the bottom support plate, said load cells being arranged at a know relationship to, but spaced from the central axis to indicate eccentricity of the center of loading relative to the central axis.

15. The apparatus of claim 14 and a primary load cell for measuring the load applied to the end surface of a specimen being tested, the friction that is present between such specimen and the side plates thereby being capable of being determined by measuring the differential in load at the load cells measuring loads on the bottom support plate and the primary load cell.

* * * * *

UNITED STATES PATENT AND TRADEMARK OFFICE
CERTIFICATE OF CORRECTION

PATENT NO. : 4,825,700
DATED : May 2, 1989
INVENTOR(S) : Ioannis G. Vardoulakis et al.

It is certified that error appears in the above-identified patent and that said Letters Patent is hereby corrected as shown below: On the title page:

In the References Cited Section, add the following:

FOREIGN PATENT DOCUMENTS 881195    11/1981    U.S.S.R.

OTHER PUBLICATIONS

"Biaxial Apparatus for Testing Shear Bands in Soils," X ICSMFE, Stockholm, 4/61, pp. 819-824 (I. Vardoulakis and M. Goldscheider (1981)).

Column 10, line 38, delete "know", insert --known--.

Signed and Sealed this

Tenth Day of April, 1990

Attest:

HARRY F. MANBECK, JR.

*Attesting Officer*     *Commissioner of Patents and Trademarks*